United States Patent
Ono et al.

(10) Patent No.: US 6,433,199 B1
(45) Date of Patent: *Aug. 13, 2002

(54) QUINONE DERIVATIVES

(75) Inventors: Mitsunori Ono, Lexington; Keizo Koya, Brookline, both of MA (US); Lijun Sun, Decatur, AL (US); Yumiko Wada, Waltham, MA (US); Wojciech Wrona, Brookline, MA (US); Natalie Dales; Xueliang Tao, both of Arlington, MA (US); Sylvia Holden, Woburn, MA (US)

(73) Assignee: Shionogi BioResearch Corporation, Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/316,190

(22) Filed: May 21, 1999

Related U.S. Application Data
(60) Provisional application No. 60/086,429, filed on May 22, 1998.

(51) Int. Cl.[7] ............................................. C07D 235/02
(52) U.S. Cl. ..................... 552/500; 548/516; 548/302.7
(58) Field of Search ............................... 548/516, 302.7

(56) References Cited

U.S. PATENT DOCUMENTS

| | | | |
|---|---|---|---|
| 5,571,845 A | 11/1996 | Denny et al. | 514/619 |
| 5,602,278 A | 2/1997 | Kirkpatrick | 562/452 |
| 5,969,133 A | * 10/1999 | Ono et al. | 544/165 |

FOREIGN PATENT DOCUMENTS

| | | | |
|---|---|---|---|
| WO | WO 96/22277 | 7/1996 | C07C/275/32 |

OTHER PUBLICATIONS

Beall et al., "Metabolism of Bioreductive Antitumor Compounds by Purified Rat and Human DT–Diaphorases", Cancer Research 54:3196–3201, 1994.

Garzon–Aburbeh et al., "1,3–Dipalmitoylglycerol Ester of Chlorambucil as a Lymphotropic, Orally Administrable Antineoplastic Agent" J. Med. Chem. 26:1200–1203, 1983.

Lin et al., "Potential Bioreductive Alkylating Agents. 5. Antineoplastic Activity of Quinoline–5,8–diones, Naphthazarins and Naphthoquinones" J. Med. Chem. 18:917–921, 1975.

Lin et al., "Potential Bioreductive Alkylating Agents. 3. Synthesis and Antineoplastic Activity of Acetoxymethyl and Corresponding Ethyl Carbamate Derivatives of Benzoquinones" J. Med. Chem. 17:558–561, 1974.

Lin et al., "Potential Bioreductive Alkylating Agents. 2. Antitumor Effect and Biochemical Studies of Naphthoquinone Derivatives" J. Med. Chem. 16:1268–1271, 1973.

Lin et al., "Potential Bioreductive Alkylating Agents. 1. Benzoquinone . . . " J. Med. Chem. 15:1247–1252, 1972.

O'Brien et al., "Differential Cytotoxicity of Diaziquone toward Chinese Hamster Ovary Cells Under Hypoxic and Aerobic Exposure Conditions" Cancer Research 50:1516–1520, 1990.

Oostveen et al., "Mitomycin Analogs I. Indoloquinones as (Potential) Bisalkylating Agents" Tetrahedron 43:255–262, 1987.

O'Shea et al., "Pulse Radiolytic Kinetic Study of the Decay of α–Methyl–Substituted Benzoquinone Radical Anions: A Possible Mechanistic Model for Bioreductive Alkylation" J. Am. Chem. Soc. 113:611–615, 1991.

Wilson et al., "Hypoxia–Selective Antitumor Agents. 2. Electronic Effects of 4–Substituents on the Mechanisms of Cytotoxicity and Metabolic Stability of Nitracrine Derivatives" J. Med. Chem. 32:31–38, 1989.

Wilson et al., "Hypoxia–Selective Antitumor Agents. 1. Relationships Between Structure, Redox Properties and Hypoxia–Selective Cyctoxicity for 4–Substituted Derivatives of Nitracrine" J. Med. Chem. 32:23–30, 1989.

Database Caplus on STN, Acc. No. 1983:594554, Witiak et al., "Bis(bioreductive) alkylating agents: synthesis and biological activity in a nude mouse human carcinoma model", J. Med. Chem. 26:1679–1686, 1883, Abstract.

* cited by examiner

Primary Examiner—Sabiha Qazi
(74) Attorney, Agent, or Firm—Fish & Richardson P.C.

(57) ABSTRACT

The invention relates to a quinone derivative of the following formula:

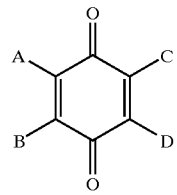

which is capable of converting into two alkylating agents upon bioreduction. Substituents A, B, C, and D are as described herein.

8 Claims, No Drawings

QUINONE DERIVATIVES

This application claims priority of U.S. provisional application No. 60/086,429, filed May 22, 1998.

BACKGROUND OF THE INVENTION

Based on the statistics provided by the American Cancer Society, approximately four million people have died from cancer since 1990, and cancer, after heart disease, is the second leading cause of death in the United States. Treatments of cancer usually include chemotherapy, radiation, hormones, immunotherapy, and surgery. Chemotherapy remains a preferred treatment, especially in cancer types that are in inoperable or metastatic forms.

Many cytotoxic agents, including antimetabolites, antibiotics, alkylating agents, and mitotic inhibitors, are now available in chemotherapy. These agents usually destroy both normal and tumor cells. It is desirable to develop an antitumor agent that preferentially destroys tumor cells over normal cells.

Due to their pathological conditions, tumor cells differ from normal cells in that their surrounding blood vessels are poorly organized, resulting in inefficient delivery of oxygen to the tumor site. In other words, tumor cells are hypoxic (oxygen deficient). This unique physiology opens the door to the design of cytotoxic agents that are specific for tumor cells.

SUMMARY OF THE INVENTION

An aspect of this invention relates to a cytotoxic compound which consists of three components: (1) a proactive alkylating moiety containing an electron-withdrawing group; (2) a bioreductive moiety containing at least two double bonds; and (3) a linker joining together the proactive alkylating moiety and the bioreductive moiety. A "proactive alkylating moiety" refers to a functional group which, once activated, replaces an active hydrogen atom of another compound, such as DNA, with one of its alkyl groups in a covalent manner. A "bioreductive moiety" refers to a moiety that is capable of undergoing an in vivo reduction (electron-accepting reaction), i.e., bioreduction. The double bonds of the bioreductive moiety, either by themselves, or together with that of the linker, form a conjugated system. The conjugated system allows electrons to flow from the bioreductive moiety to the electron-withdrawing group of the proactive alkylating moiety upon reduction of the bioreductive moiety. This results in breaking the bond between the electron-withdrawing group and the linker and converting the proactive alkylating moiety into an active alkylating compound.

An example of the proactive alkylating moiety is an aromatic group (e.g., phenyl group or naphthyl) substituted with an electron-withdrawing group (e.g., ester, urethane, or carbonate) and a bis(haloethyl)amino group (e.g., a bis (chloroethyl)amino group or nitrogen mustard). The bis (haloethyl)amino group, upon bioreduction, becomes an alkylating group. When the aromatic moiety is a phenyl, each of the two substituents is preferred to be at a meta or para position with respect to each other. Each of the remaining positions of the phenyl, independently, is optionally substituted with alkyl, alkenyl, aryl, aralkyl, heteroaryl, heteroaralkyl, amino, aminoalkyl, hydroxyl, hydroxylalkyl, alkoxy, aryloxy, aralkoxy, heteroaryloxy, heteroaralkoxy, oligoalkylene glycol, amido, ester, aralkoxycarbonylamino, ureido, thio, alkylthio, arylthio, or heteroarylthio. Among them, alkyl, alkoxy, oligoalkylene glycol, aryloxy, heteroaryloxy, and amino are preferred. It is preferable that each of these substituents is at an ortho position with respect to the bis(haloethyl)amino group.

The bioreductive moiety is converted into a second alkylating agent upon bioreduction. Some examples of the bioreductive moiety are 1,4-benzoquinone (i.e., quinone), nitrobenzene, or 1,2-dioxocyclohex-3,5-diene. When the bioreductive moiety is quinone, each of the non-oxo positions of the quinone ring, independently, is optionally substituted with alkyl, alkenyl, aryl, aralkyl, heteroaryl, heteroaralkyl, amino, aminoalkyl, hydroxyl, hydroxylalkyl, alkoxy, aryloxy, aralkoxy, heteroaryloxy, heteroaralkoxy, carboxylate, acyloxyalkyl, ester, amido, amidoalkyl, sulfoamido, sulfonylamino, thio, alkylthio, arylthio, aralkylthio, heteroarylthio, or heteroaralkylthio. The preferred substituents are alkyl, amino, aminoalkyl, alkoxy, hydroxylalkyl, and acyloxyalkyl. If both 2-C and 3-C positions or both 5-C and 6-C positions of the quinone are substituted, the two substituents optionally together form a ring. Two fused rings can be formed with the quinone ring if all non-oxo positions of the quinone are substituted and each pair of the substituents together form a fused ring. The fused ring can be either aliphatic or aromatic. It is also optionally substituted with alkyl, alkenyl, aryl, aralkyl, heteroaryl, heteroaralkyl, amino, aminoalkyl, hydroxyl, hydroxylalkyl, alkoxy, aryloxy, aralkoxy, heteroaryloxy, heteroaralkoxy, carboxylate, acyloxyalkyl, ester, amido, amidoalkyl, sulfoamido, sulfonylamino, thio, alkylthio, arylthio, aralkylthio, heteroarylthio, or heteroaralkylthio. The fused ring optionally contains 1–3 heteroatoms, such as nitrogen, oxygen, or sulfur.

The linker which links the proactive alkylating moiety and the bioreductive moiety together can be one of the following: a methylene group, a $C_3$ hydrocarbon chain containing a double bond, or a $C_5$ hydrocarbon chain containing two alternate double bonds. This linker is optionally substituted with alkyl, alkenyl, aryl, aralkyl, heteroaryl, heteroaralkyl, or oligoalkylene glycol. If the linker contains more than two substituents, two of them can join together to form a 5–6 membered ring. The ring can be aliphatic or aromatic and is optionally substituted with alkyl, alkenyl, aryl, aralkyl, heteroaryl, heteroaralkyl, or oligoalkylene glycol. One to three heteroatoms such as nitrogen, oxygen, or sulfur, can form part of the ring.

A salt of a cytotoxic compound is also within the scope of this invention. For example, the salt can be formed between an amino substituent of a cytotoxic compound and a negatively charged counterion. Suitable counterions include, but are not limited to, chloride, hydrochloride, bromide, iodide, sulfate, nitrate, phosphate, or acetate. Likewise, a negatively charged substituent, e.g., carboxylate, of a compound of this invention can also form a salt with a cation, e.g., an alkali metal cation such as sodium ion or potassium ion; an alkaline earth metal cation such as magnesium cation or calcium cation; or an ammonium cation that can be substitued with one or more organic groups such as tetramethylammonium ion or diisopropylethylammonium ion.

The term "alkyl" in this disclosure denotes a straight or branched hydrocarbon chain containing 1 to 8 carbon atoms, or cyclic hydrocarbon chain containing 3 to 8 carbon atoms. The cyclic hydrocarbon chain may contain 1–3 heteroatoms such as nitrogen, oxygen, or sulfur and may also contain fused rings. Fused rings are rings that share a common carbon-carbon bond. Examples of alkyl include, but are not limited to, methyl, ethyl, propyl, isopropyl, butyl, isobutyl, sec-butyl, tert-butyl, amyl, isopentyl, hexyl, isohexyl, heptyl, octyl, cyclopropyl, cyclopentyl, cyclohexyl, cycloheptyl, norbornyl, isobornyl, cyclohexylmethyl, 1- or 2-cyclohexylethyl, 1-, 2-, or 3-cyclohexylpropyl, tetrahydrofuranyl, tetrahydropyranyl, piperidinyl, morpholino and pyrrolindinyl groups.

By the term "alkenyl" is meant a straight or branched hydrocarbon chain containing 2 to 8 carbon atoms or cyclic hydrocarbon chain, i.e., "cycloalkenyl," containing 3 to 8 carbon atoms, which is characterized by having one or more double bonds. The cycloalkenyl may contain 1–3 heteroatoms such as nitrogen, oxygen, or sulfur, i.e., "heterocycloalkenyl," and may also contain fused rings. Typically alkenyl groups include allyl, 2-butenyl, 2-pentenyl, 2-hexenyl, cyclopropenyl, cyclopentenyl, cyclohexenyl, cycloheptenyl, cyclo-octenyl, and norbornylenyl.

"Aryl" is an cyclic aromatic moiety containing 3–8 carbon atoms and may also contain fused rings. Fused aryl denotes an aromatic ring that shares a common carbon-carbon bond with another cyclic moiety. This cyclic moiety can be either an aryl, a cycloalkyl, or a heterocycloalkyl. Typically aryl groups include phenyl, 1-naphthyl, 2-naphthyl, biphenyl, phenanthryl, and anthracyl groups. "Heteroaryl" refers to aryl groups that contains 1–3 heteroatoms. Typically heterocyclic aromatic rings including coumarinyl, pyridyl, pyrazinyl, pyrimidyl, furyl, pyrrolyl, thienyl, thiazolyl, oxazolyl, imidazolyl, indolyl, benzofuranyl and benzthiazolyl. An example of the aralkyl group is 2-phenylethyl.

The term "oligoalkylene glycol" refers to a chain of 2–5 alkoxy groups. Each of the alkoxy groups may or may not be identical. An example of an oligoalkylene glycol is ethoxymethoxy.

As used herein, substituents such as amino, amido, ester, sulfoamido, sulfonylamino, and ureido are either unsubstituted or substituted with alkyl, alkenyl, aryl, aralkyl, heteroaryl, or heteroaralkyl. Further, a divalent substituent such as amido or ester can be connected to its two neighboring moieties in either orientation. The substituents of a cyclic group, e.g., phenyl, can be attached at any available position.

Another aspect of this invention relates to a composition which contains one of the cytotoxic compounds (or its salt) described above and a pharmaceutically acceptable carrier. The compound is in an amount which is effective for treating tumors. Still another aspect of this invention relates to a method of treating tumors, which comprises administering to a patient in need thereof an effective amount of such a cytotoxic compound or its salt. Some examples of tumors which can be treated by this method are leukemia, lung cancer, colon cancer, CNS cancer, melanoma, ovarian cancer, renal cancer, prostate cancer, and breast cancer. The use of such a cytotoxic compound for the manufacture of a medicament for treating the above-mentioned tumors is also within the scope of this invention.

Other features and advantages of the present invention will be apparent from the following description of the preferred embodiments, and also from the appending claims.

DETAILED DESCRIPTION OF THE INVENTION

The present invention relates to a cytotoxic compound which has (1) a proactive alkylating moiety containing an electron-withdrawing group and (2) a bioreductive moiety.

Examples of the bioreductive moiety include:

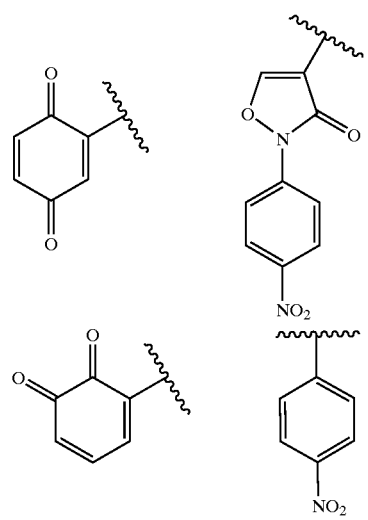

Examples of the proactive alkylating moiety include:

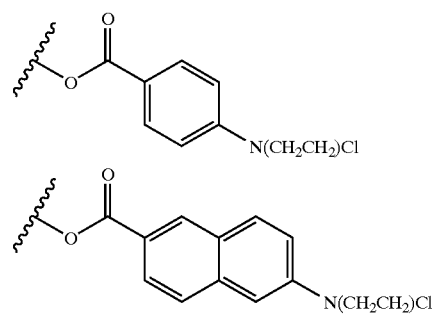

Note that in both of the above examples, the ester group of the proactive alkylating moiety is the electron-withdrawing group.

As mentioned above, a cytotoxic compound disclosed in this invention is capable of converting into two alkylating agents upon bioreduction. The mechanism of this conversion can generally be divided into two stages. A cytotoxic compound containing quinone as the bioreductive moiety, methylene group as the linker, and bis(chloroethyl)-aminophenyl ester as the proactive alkylating moiety is used as an example in the following description.

The first stage involves the reduction of the bioreductive moiety. Typically, this is achieved by cellular enzymes, e.g., cytochrome $P_{450}$ reductase. Quinone can undergo bioreduction in two one-electron steps, which produces a semiquinone radical anion in the first seduction, and a hydroquinone in the second one. The semiquinone radical anion is very reactive towards oxygen. Indeed, in normal tissues where there is an abundance of oxygen, most of the radical anions are re-oxidized back to quinone.

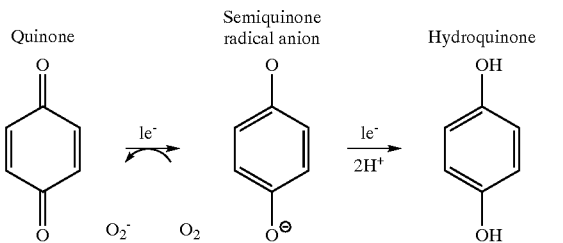

As mentioned in the background section, a tumor site is characterized by its poorly organized vascular system, which results in a generally more hypoxic (oxygen-deficient) environment in comparison to that of normal tissues. In other words, reduced compounds are less likely to encounter molecular oxygen and be re-oxidized. Semiquinone radical anions, therefore, have longer halflife and can be further reduced to produce hydroquinone.

In the second stage, a pair of electrons travel from the oxygen of the hydroquinone to the quinone ring (see illustration shown below, where the electron-withdrawing group is —O—(C=O)— (ester) and the linker is a —CH$_2$— (methylene)), and finally to the oxygen of the electron-withdrawing group of the proactive alkylating moiety via the linker which joins the bioreductive and the proactive alkylating moieties. This electron travelling activity thus results in cleavage of the bond between the electron-withdrawing group and the linker, thereby converting the quinone moiety into a quinone methide. Quinone methides are known alkylating agents capable of attacking nucleophiles, e.g., DNA (See Lin et al., J. Med. Chem. 1972, 15, 127; J. Med. Chem. 1973, 16, 1268; J. Med. Chem. 197, 17, 688; J. Med. Chem. 1975, 18, 917; J. Med. Chem. 1976, 19, 1336). quinone methide

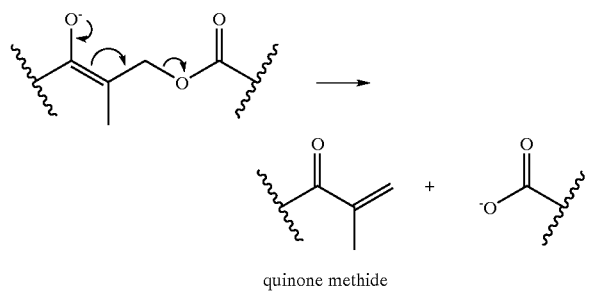

As a consequence of this bond cleavage, the electron-withdrawing group is converted into one that is much less electron-withdrawing. This conversion, in turn, increases the electron density of the bis(haloethyl)amino group and converts the proactive alkylating moiety into an alkylating agent. Using an ester group as an example, its strong electron-withdrawing character, as indicated by the Hammet substitution constants ($\sigma_p$=0.45 and $\sigma_m$=0.37) keeps the bis(chloroethyl)amino alkylating moiety in a deactivated stage. As the ester group is converted into a carboxylate, which is much less electron-withdrawing (with $\sigma_p$=0 and $\sigma_m$=−0.1), the electron density of the amino nitrogen of the bis(haloethyl)amino increases, thus resulting in a boost in its alkylating activities.

A class of cytotoxic compounds of this invention is represented by formula (I) below:

wherein each of A, B, C, and D, independently, is —R$^1$, —R—NR$^1$R$^2$, —O—R$^1$, —R—OH, —C(=O)O—R$^1$, —R—O—C(=O)R$^1$, —C(=O)—NR$^1$R$^2$, —R—NR$^1$—C(=O)R$^2$, —SO$_2$—NR$^1$R$^2$, —N=SO$_2$, —S—R$^1$, or —L—W—Ph—N(CH$_2$CH$_2$X)$_2$. Optionally, A and B together form a 5–6 membered fused ring with the quinone ring, if none of A and B is —L—W—Ph—N(CH$_2$CH$_2$X)$_2$. Similarly, C and D optionally join together to form a 5–6 membered fused ring with the quinone ring, if none of C and D is —L—W—Ph—N(CH$_2$CH$_2$X)$_2$. The fused ring optionally contains 1–3 heteroatoms such as nitrogen, oxygen, or sulfur, and can optionally substituted with alkyl, alkenyl, aryl, aralkyl, heteroaryl, heteroaralkyl, —R—NR$^1$R$^2$, —O—R$^1$, —R—OH, —C(=O)O—R$^1$, —R—O—C(=O)R$^1$, —C(=O)—NR$^1$R$^2$, —R—NR$^1$—C(=O)R$^2$, —SO$_2$—NR$^1$R$^2$, —N=SO$_2$, or —S—R$^1$. Each R, independently, is alkyl or deleted. Each of R$^1$ and R$^2$, independently, is hydrogen, alkyl, alkenyl, aryl, aralkyl, heteroaryl, or heteroaralkyl. L is —(CR$^3$=CR$^4$)$_n$—CR$^5$R$^6$—, in which each of R$^3$, R$^4$, R$^5$, and R$^6$, independently, is hydrogen, alkyl, alkenyl, aryl, aralkyl, heteroaryl, heteroaralkyl, or —(O-alkyl)$_{1-5}$; and n is 0, 1, or 2. The term "—(O-alkyl)$_{1-5}$" refers to an alkoxy group ("—(O-alkyl)$_1$") or an oligoalkylene glycol group ("—(O-alkyl)$_{2-5}$"). R$^3$ and R$^4$, when n is not 0, optionally form a 5- to 6-membered ring together. The ring can be aliphatic or aromatic and can optionally substituted with alkyl, alkenyl, aryl, aralkyl, heteroaryl, heteroaralkyl, or —(O-alkyl)$_{1-5}$. 1–3 heteroatoms, e.g., nitrogen, oxygen, or sulfur, can also form part of the ring. W is —O—C(=O)—, —O—C(=O)—NR$^1$—, or —O—(=O)O—. Ph is a phenyl group, optionally substituted with alkyl, alkenyl, aryl, aralkyl, heteroaryl, heteroaralkyl, —R—NR$^1$R$^2$, —OH, —(O-alkyl)$_{1-5}$, —O-aryl, —O-aralkyl, —O-heteroaryl, —O-heteroaralkyl, —R—OH, —C(=O)O—R$^1$, —O—C(=O)R$^1$, —C(=O)—NR$^1$R$^2$, —NR$^1$—C(=O)R$^2$, —NR$^1$—C(=O)O—R$^2$, —NR$^1$—C(=O)NR$^1$R$^2$, or —S—R$^1$. X is a halo, e.g., fluoro, chloro, bromo, or iodo.

Note that if neither A and B, nor C and D, form a fused ring with the quinone ring, then at least one of A, B, C, or D is —L—W—Ph—N(CH$_2$CH$_2$X)$_2$. Further, if none of A, B, C, and D is —L—W—Ph—N(CH$_2$CH$_2$X)$_2$, then A and B, or C and D (including A and B, as well as C and D) together form a fused ring with the quinone ring. The fused ring (or at least one of the two fused rings if two fused rings are present) contains a double bond between two ring atoms and is substituted with —L—W—Ph—N(CH$_2$CH$_2$X)$_2$ at one of the two ring atoms. This double bond, together with the double bonds of the quinone ring, form a conjugated system to allow electron to flow from one double bond to another.

Some specific examples of a compound of formula (I) are shown below.

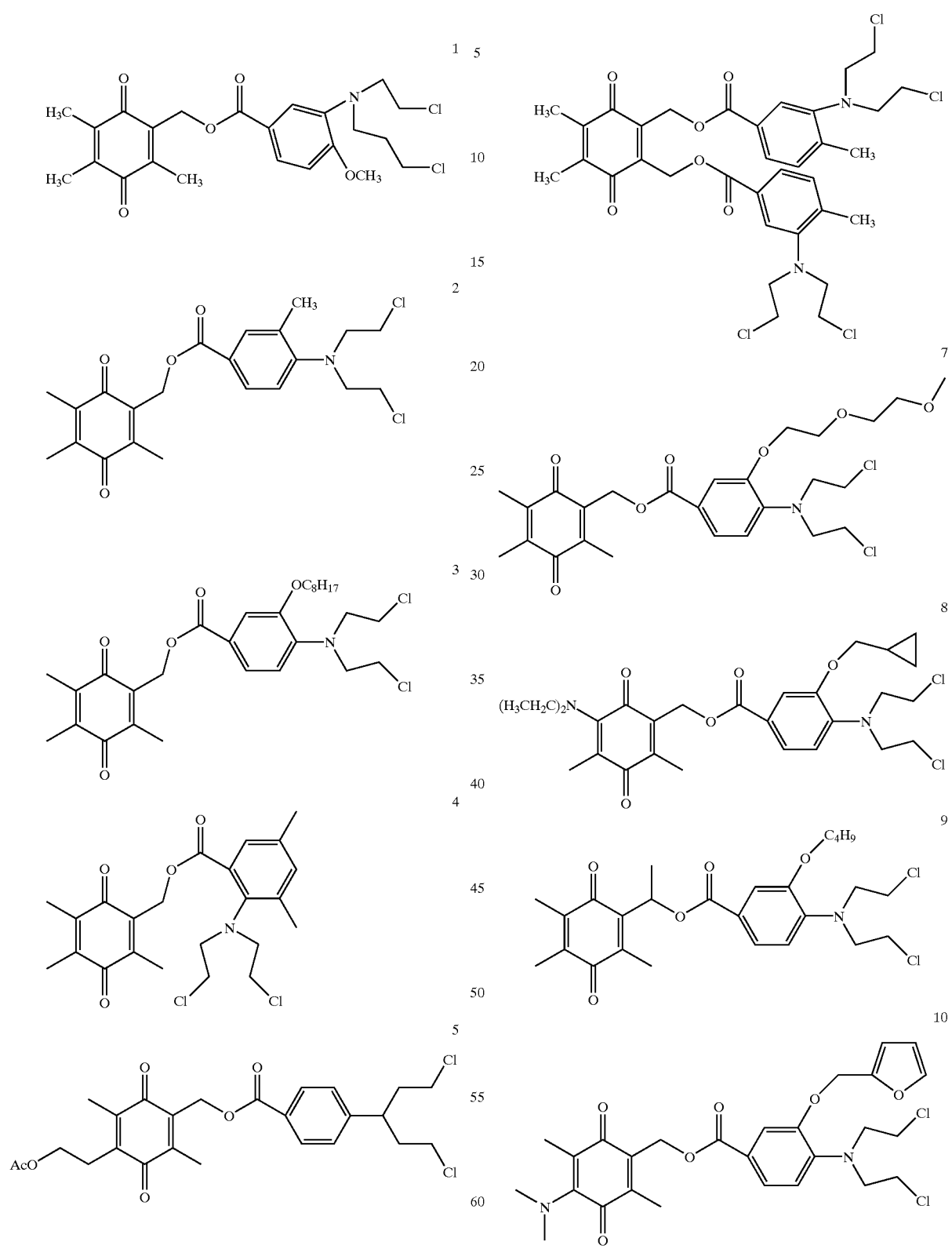

-continued

-continued

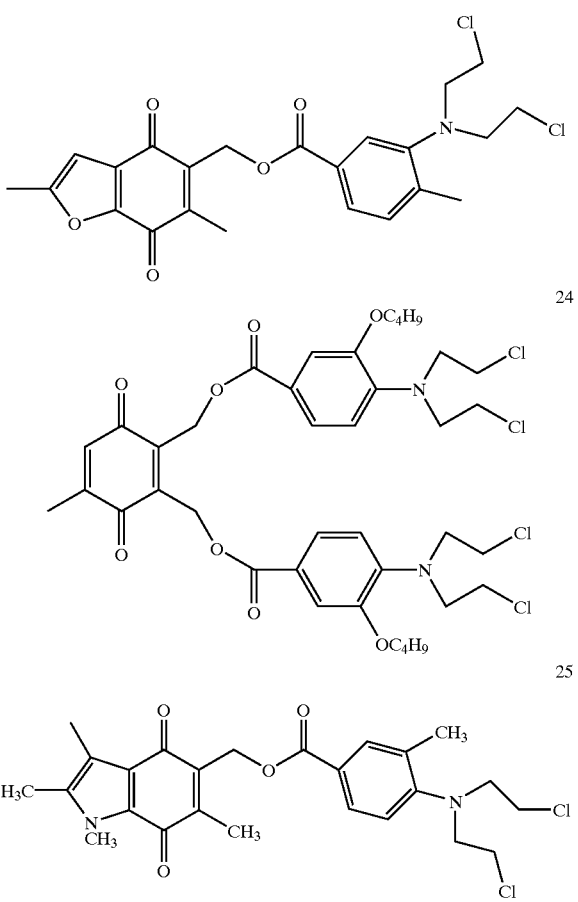

The preparation of a compound of formula (I) is generally divided into three parts: (1) the preparation of a bioreductive quinone moiety; (2) the preparation of a bis(haloethyl) amino-phenyl moiety; and (3) coupling of the bioreductive quinone moiety and the bix(haloethyl)amino-phenyl moiety. The general synthetic procedures of parts (1)–(3) are described below:

(1) Preparation of a quinone-ring containing bioreductive moiety:

A leaving group, e.g., a halide, that is attached to the linker of a properly protected bioreductive moiety is necessary to couple to a desired bis(haloethyl)amino- containing phenyl moiety in part (3). The leaving group and the linker can be introduced at a non-oxo position of the quinone ring by, e.g., electrophilic substitution reaction. As illustrated in part (1) of Example 1, a hydroxymethyl group resulted at the $C_2$ carbon of 3,5,6-trimethyl-hydroquinone dimethyl ester as the hydroquinone reacted with paraformaldehyde. Since the reaction took place in hydrochloric acid, the hydroxylmethyl reacted further and resulted in the hydroxyl group being replaced with chloride ion. This reaction thus produced a chloromethyl-substituted quinone. The two methyl ester protecting groups were then be deprotected afterwards by hydrolysis.

(2) Preparation of a bis(haloethyl)amino-containing phenyl moiety (chloro is the halo in the following description):

A bis(chloroethyl)amino phenyl moiety can be prepared from, e.g., a nitrobenzoic acid. The carboxylate can be protected in the form of an ester. Suitable substituents to the benzene ring can be coupled to or transformed at this point, e.g., see part (2) of Example 1. The nitro group can then be reduced to form an amino group. This amino group can then react with an ethylene oxide, forming a disubstituted hydroxyethyl amino group. The alkylating moiety, i.e., the bis(chloroethyl)amino moiety, is finally formed when a chlorination agent, e.g., thionyl chloride, is added to the bis(hydroxyethyl)amino-containing intermediate. Similar to the deprotection reaction in part (1), the ester group is being cleaved by hydrolysis.

(3) Coupling reaction of the quinone ring-containing bioreductive moiety and the bis(chloroethyl)amino-containing phenyl moiety:

In a typical example, a quinone ring-containing moiety, e.g., 2-chloromethyl-3,5,6-trimethylbenzoquinone in Example 1, can be coupled to a bis(chloroethyl)amino-containing phenyl moiety, e.g., 3-[bis-(2-chloroethyl)amino-4-methoxybenzoic acid, via a nucleophilic substitution reaction. The carboxylate, which acts as a nucleophile, displaces the halide ion and results in the formation of an ester linkage.

As mentioned above, a pharmaceutical composition of this invention containing a cytotoxic compound in an effective amount can be used to treat tumors. Also within the scope of this invention is a method of treating tumor by administering to a patient such a composition. An effective amount of a cytotoxic compound (or a salt of the cytotoxic compound) is defined as the amount of the compound which, upon administration to a patient in need, confers a therapeutic effect on treated patient. The effective amount to be administered to a patient is typically based on age, surface area, weight, and conditions of the patient. The interrelationship of dosages for animals and humans (based on milligrams per meter squared of body surface) is described by Freireich et al., Cancer Chemother. Rep. 1966, 50, 219. Body surface area may be approximately determined from height and weight of the patient. See, e.g., Scientific Tables, Geigy Pharmaceuticals, Ardley, N.Y., 1970, 537. An effective amount of a cytotoxic compound used to practice the invention can range from about 0.1 mg/kg to about 250 mg/kg. Effective doses will also vary, as recognized by those skilled in the art, dependant on route of administration, excipient usage, and the possibility of co-usage with other therapeutic treatments including use of other antitumor agents and radiation therapy.

The pharmaceutical composition may be administered via the parenteral route, including orally, topically, subcutaneously, intraperitoneally, intramuscularly, and intravenously. Examples of parenteral dosage forms include aqueous solutions of the active agent, in a isotonic saline, 5% glucose or other well-known pharmaceutically acceptable excipient. Solubilizing agents such as cyclodextrins, or other solubilizing agents well-known to those familiar with the art, can be utilized as pharmaceutical excipients for delivery of the therapeutic compounds.

A cytotoxic compound of this invention can also be formulated into dosage forms for other routes of administration utilizing well-known methods. The pharmaceutical composition can be formulated, for example, in dosage forms for oral administration in a capsule, a gel seal or a tablet. Capsules may comprise any well-known pharmaceutically acceptable material such as gelatin or cellulose derivatives. Tablets may be formulated in accordance with the conventional procedure by compressing mixtures of the active compounds of the present invention and a solid carrier, and a lubricant. Examples of solid carriers include starch and sugar bentonite. The cytotoxic compound can also be administered in a form of a hard shell tablet or capsule containing, for example, lactose or mannitol as a binder and a conventional filler and a tableting agent.

The antitumor activity of the compounds of this invention can be preliminarily evaluated by using a tumor growth regression assay which assesses the ability of tested compounds to inhibit the growth of established solid tumors in mice. The assay can be performed by implanting tumor cells into the fat pads of nude mice. Tumor cells are then allowed to grow to a certain size before the cytotoxic compounds are administered. The volumes of tumor are then monitored for a set number of weeks, e.g., three weeks. General health of the tested animals are also monitored during the course of the assay.

Without further elaboration, it is believed that one skilled in the art can, based on the description herein, utilize the present invention to its fullest extent. The following specific examples, which described syntheses and biological testings of various compounds of the present invention, are therefore, to be construed as merely illustrative, and not limitative of the remainder of the disclosure in any way whatsoever, All publications recited herein, including patents, are hereby incorporated by reference in their entirety.

Each of the examples 1–7 depicts in detail the synthesis of seven cytotoxic compounds of this invention. Each example is divided into three parts: (1) the preparation of a bioreductive quinone moiety, (2) the preparation of a bis(chloroethyl)amino-phenyl moiety, and (3) the coupling reaction of these two moieties.

EXAMPLE 1

Synthesis of Compound 1

(1) Synthesis of 2-chloromethyl-3,5,6-trimethylbenzoquinone

Hydrogen chloride gas was introduced to the mixture of 3,5,6-trimethylhydroquinone dimethylether (1 g, 5.5 mmol) and paraformaldehyde (1 g) in acetic acid containing 1N HCl (30 mL). Then the reaction mixture was stirred at 60° C. for 1 hour. The mixture was poured into 400 mL of water and then filtrated. The residue was dissolved in 100 mL of ethyl acetate and washed with saturated NaCl solution (100 mL). The extracts was dried over magnesium sulfate and the solvent was removed under reduced pressure. Methyl 4-2-chloromethyl-3,5,6-trimethylhydroquinone dimethylether was obtained as a white solid (0.8 g, 6%). $^1$H NMR (300 MHz, CDCl$_3$): 4.47 (s, 2H), 3.79 (s, 3H), 3.66 (s, 3H), 2.3 (s, 2H), 2.20 (s, 3H), 2.18 (s, 3H). ESMS Calc. for Cl$_2$H$_{19}$ClO$_2$: 230.73; Found: 231.7 (M+H)$^+$.

0.8 g (3.5 mmol) of 2-chloromethyl-3,5,6-trimethylhydroquinone dimethylether was dissolved in 20 mL of acetonitrile. After addition of 9.6 g of ammonium cerium (IV) nitrate in 200 mL of water to the solution, the mixture was extracted with ethyl acetate (100 mL and 50 mL). The combined extract dried over magnesium sulfate and the solvent was removed under reduced pressure. 50 mL of water was added to the residue and then the mixture was extracted with ethyl acetate (50 mL). The extract was washed with saturated NaCl solution (100 mL). The extract dried over magnesium sulfate and the solvent was removed under reduced pressure to give 2-chloromethyl-3,5,6-trimethylbenzoquinone as a yellow crystal. $^1$H NMR (300 MHz, CDCl$_3$) 4.47 (s, 2H) 2.16 (s, 3H), 2.06 (s, 3H), 2.05 (s, 3H). ESMS: Calc. for C$_{10}$H$_{11}$ClO$_2$: 198.65; Found: 199.6 (M+H)$^+$.

(2) Synthesis of 3-bis(2'-chloroethyl)amino-4-methoxybenzoic acid

The reaction mixture of methyl 3-amino-4-methoxybenzoate (10.94 g, 0.06 mol) and ethylene oxide (12.5 g, 0.28 mol) in acetic acid (150 mL) was stirred at room temperature for 24 hours. Then it was concentrated to about 80 mL on a rotary evaporator, diluted with H$_2$O (300 mL), extracted with dichloromethane/ethyl acetate (1:1, 6×300 mL). The organic solution was concentrated to give an off-white oil (8.6 g, 54%). $^1$H NMR (300 MHz, CDCl$_3$): 7.85 (m, 2H), 6.94 (d, J=8.1 Hz, 1H), 3.90 (s, 3H), 3.84 (s, 3H), 3.52 (m, 4H), 3.24 (m, 4H).

Thionyl chloride (1.2 mL) was added slowly to a benzene solution (40 mL) of methyl 3-(2'-bis(hydroxyethyl)amino)-4-methoxybenzoate (2.80 g, 10.40 mmol) stirred at room temperature. After the addition, the reaction slurry was heated to reflux for 0.5 hour. The reaction mixture was then treated with ice/H$_2$O (100 mL) and extracted with ethyl acetate (100 mL). The ethyl acetate solution was washed with sodium bicarbonate (100 mL), dried over magnesium sulfate, and concentrated to furnish the product as an off-white solid (2.50 g, 79%). $^1$H NMR (300 MHz, CDCl$_3$): 7.76 (dd, J=8.4, 2.4 Hz, 1H), 7.69 (d, J=2.4 Hz, 1H), 6.90 (d, J=8.4 Hz, 1H), 3.90 (s, 3H), 3.85 (s, 3H), 3.52 (s, 8H). ESMS calcd for C$_{13}$H$_{17}$Cl$_2$NO$_3$: 305.1; Found: 328.0 (M+Na)$^+$.

A suspension of methyl 3-bis(2'-chloroethyl)amino-4-methoxybenzoate (2.70 g, 8.823 mmol) in concentrated HCl (37% w/w in H$_2$O, 40 mL) was heated to reflux under N2 for 1 hour. The reaction mixture was treated with ice/H$_2$O (200 mL), extracted with ethyl acetate (4×150 mL). The organic solution was concentrated to give a white solid (2.05 g, 80%). ESMS calcd for C$_{12}$H$_{15}$Cl$_2$NO$_3$: 291.0; Found: 292.0 (M+H)$^+$.

(3) Coupling of intermediates from (1) and (2)

An acetone solution (25 mL) of 3-bis(2'-chloroethyl)amino-4-methoxybenzoic acid (0.51 g, 1.750 mmol) and 2-chloromethyl-3,5,6-trimethylbenzoquinone (0.56 g, 2.819 mmol) was heated to reflux for 2 hours under N$_2$ in the presence of potassium carbonate (2.0 g) and sodium iodide (1.2 g). The organic layer was separated, diluted with ethyl acetate (50 mL), washed with aqueous potassium carbonate (2×50 mL), dried over magnesium sulfate, and concentrated to an oil. Flash chromatography purification on silica gel furnished the product as sticky oil (0.61 g, 77%). $^1$H NMR (300 MHz, CDCl$_3$): 7.70 (dd, J=8.4, 1.8 Hz, 1H), 7.65 (d, J=1.8 Hz, 1H), 6.86 (d, J=8.4 Hz, 1H), 5.25 (s, 3H), 3.90 (s, 3H), 3.50 (s, 8H), 2.18 (s, 3H), 2.06 (s, 3H), 2.05 (s, 3H). ESMS cacld for C$_{22}$H$_{25}$Cl$_2$NO$_5$: 453.1; Found: 454.1 (M+H)$^+$.

EXAMPLE 2

Synthesis of Compound 2

(1) See part (1) of Example 1.

(2) See part (2) of Example 1, except that the starting material is 3-amino-4-methylbenzoate instead of 3-amino-4-methoxybenzoate.

(3) Coupling of intermediates from (1) and (2)

3-Methyl-4-bis(2'-chloroethyl)aminobenzoic acid (830 mg, 3.02 mmol) and 2-chloromethyl-3,5,6-trimethylbenzoquinone (500 mg, 2.51 mmol) were dissolved in acetone (20 mL) and heated to 500° C. in the presence of potassium carbonate (1 g) and sodium iodide (80 mg) for 1.5 hours. The mixture was poured into 300 mL of water and extracted with ethyl acetate (100 mL, 4 times). The extract was dried over magnesium sulfate and then concentrated under reduced pressure. Quinone-mustard A was obtained as an oil (800 mg, 72%). $^1$H NMR (300 MHz, CDCl$_3$): 7.75 (dd, J=2.19, 2.19 Hz, 1H), 7.63 (m, 1H), 6.65 (d, J=8.52, 1H), 5.22 (s, 2H), 3.48 (m, 8H), 2.31 (s, 3H), 2.15 (s, 3H) 2.14 (s, 3H), 2.04 (s, 3H), ESMS Calc for C$_{22}$H$_{25}$Cl$_2$NO$_4$: 438.31; Found: 439.0 (M+H)$^+$.

EXAMPLE 3

Synthesis of Compound 3

(1) See part (1) of Example 1.

(2) Synthesis of 4-bis(2'-chloroethyl)amino-3-octoxybenzoic acid

A slurry of methyl 3-hydroxy-4-nitrobenzoate (5.5 g, 0.028 mol), iodooctane (10.0 g, 0.042 mol) and potassium carbonate (20 g) in DMF (100 mL) was stirred at 100° C. for 3 hours. The reaction mixture was cooled to room temperature, diluted with $H_2O$ (500 mL) then extracted with ether/ethyl acetate (9/1, 2×200 mL). The combined organic solution was washed with $H_2O$ (400 mL), dried over sodium sulfate, and concentrated to an off-white oil (8.7 g, 100%).

A methanol solution (150 mL) of methyl 4-nitro-3-octoxybenzoate (8.7 g, 0.028 mol) was stirred at room temperature in the presence of 10% Pd-C under $H_2$ atmosphere for 29 h. The reaction mixture was filtered through Celite, concentrated to give an off-white solid (7.6 g, 96%). $^1H$ NMR (300 MHz, $CDCl_3$): 7.25 (d, J=2.1 Hz, 1H), MS calcd for $C_{16}H_{25}NO_3$: 279.2; Found: 279.

The reaction mixture of methyl 4-amino-3-octoxybenzoate (3.47 g, 12.4 mmol) and ethylene oxide (4.5 g, 198 mol) in acetic acid (100 mL) was stirred at room temperature for 12 hours. It was diluted with $H_2O$ (500 mL) extracted with chloroform/methanol (95/5, 4×100 mL). The organic solution was concentrated to brown oil. Flash chromatographic purification (silica gel, 5% to 10% methanol in chloroform) afforded the product as off-white oil (2.25 g, 42%). $^1H$ NMR (300 MHz, $CDCl_3$): 7.62 (dd, J=8.1, 2.1 Hz, 1H), 7.55 (d, J=2.1 Hz, 1H), 7.12 (d, J=8.4 Hz, 1H), 4.06 (t, J=6.9 Hz, 2H), 3.90 (s, 3H), 3.64 (t, J=5.1 Hz, 4H), 3.38 (t, J=5.1 Hz, 4H), 1.86 (J=5.1 Hz, 2H), 1.30 (m, 10H), 0.89 (t, J=6.9 Hz, 3H). ESMS calcd for $C_{20}H_{33}NO_5$: 367.2; Found: 390.3 (M+Na)+.

Thionyl chloride (1.2 mL, 16 mmol) was added slowly to a benzene solution (50 mL) of methyl 4-bis(2'-hydroxyethyl)amino-3-octoxybenzoate (2.20 g, 6.0 mol) stirred at room temperature. After the addition, the reaction was refluxed for 1.5 hours. The reaction mixture was cooled to room temperature, treated with ice/$H_2O$ (100 mL) and extracted with ethyl acetate (50 mL). The organic solution was washed with sodium bicarbonate (20 mL), $H_2O$ (50 mL), dried over magnesium sulfate, and concentrated to furnish the product as off-white oil (2.1 g, 87%). $^1H$ NMR (300 MHz, $CDCl_3$): 7.58 (dd, J=8.1, 1.8 Hz, 1H), 7.51 (d, J=1.8 Hz, 1H), 6.92 (d, J=8.1 Hz, 1H), 4.03 (t, J=6.6 Hz, 1H), 3.89 (s, 3H), 3.60 (m, 8H), 1.85 (J=7.2 Hz, 2H), 1.30 (m, 10H), 0.89 (t, J=6.9 Hz, 3H). ESMS calcd for $C_{20}H_{31}Cl_2NO_3$: 403.2; Found: 404.2 (M+H)+.

A suspension of methyl 4-bis(2'-chloroethyl)amino-3-octoxybenzoate (1.8 g, 4.5 mmol) in concentrated HCl (37% w/w in $H_2O$, 50 mL) was heated to reflux under N2 for 0.5 hours. The reaction mixture was treated with ice/$H_2O$ (100 mL), extracted with chloroform (3×50 mL). The organic solution was concentrated to give a brown oil. Flash chromatographic purification (silica gel, 2% methanol in chloroform) gave the product as an off-white solid (1.58 g, 88%). $^1H$ NMR (300 MHz, $CDCl_3$): 7.67 (dd, J=8.1, 1.5 Hz, 1H), 7.56 (d, J=1.5 Hz, 1H), 6.93 (d, J=8.4 Hz, 1H), 4.40 (d, J=6.6 Hz, 2H), 3.65 (m, 8H), 1.85 (J=7.8 Hz, 2H), 1.35 (m, 10H), 0.90 (t, J=6.6 Hz, 3H). ESMS calcd for $C_{29}H_{29}Cl_2NO_3$: 389.2; Found: 390.2 (M+H)+.

(3) Coupling of intermediates from parts (1) and (2)

Same procedure as described in part (3) of Examples 1 and 2. $^1H$ NMR: δ 7.76 (dd, J=8. and 1.8 Hz, 1H), 7.68 (d, J=1.8 Hz, 1H), 6.98 (d, J=8. Hz, 1H), 5.25 (s, 2H), 3.53 (brs, 8H), 3.6 (t, J=5.0 Hz, 2H), 2.18 (s, 3H), 2.0 (s, 3H), 2.02 (s, 3H), 1.86 (J=5.0 Hz, 2H), 1.30 (m, 10H), 0.89 (t, J=6.9 Hz 3H). ESMS calcd for $C_{29}H_{39}Cl_2NO_5$: 552.2; Found: 553.1 (M+H)+.

EXAMPLE 4

Synthesis of compound 4

(1) See part (1) of Example 1.

(2) Synthesis of 2-bis(2'-chloroethyl)amino-3,5-dimethylbenzoic acid

The reaction mixture of methyl 2-amino-3,5-dimethylbenzoate (7.0 g, 0.039 mol) and ethylene oxide (10 g, 0.23 mol) in acetic acid (150 mL) was stirred at room temperature for 19 hours. Then it was concentrated to about 100 mL on a rotary evaporator, diluted with $H_2O$ (300 mL), extracted with chloroform (5×200 mL). The organic solution was concentrated to give an off-white oil (10.0 g, 96%). $^1H$ NMR (300 MHz, $CDCl_3$): 7.31 (br s, 1H), 7.16 (br s, 1H), 3.91 (s, 3H), 3.73 (m, 2H), 3.63 (m, 2H), 3.26 (br m, 4H), 2.32 (s, 3H), 2.30 (s, 3H).

Thionyl chloride (12 mL, 0.16 mol) was added slowly to a benzene solution (200 mL) of methyl 2-bis(2'-hydroxyethyl)amino-3,5-dimethylbenzoate (7.0 g, 0.026 mol) stirred at room temperature. After the addition, the reaction slurry was stirred at room temperature for 12 hours. The reaction mixture was then treated with ice/$H_2O$ (500 mL) and extracted with ethyl acetate (2×300 mL). The ethyl acetate solution was washed with $H_2O$ (300 mL), sodium bicarbonate (200 mL), dried over magnesium sulfate, and concentrated to furnish the product as a clear oil (5.6 g, 71%). $^1H$ NMR (300 MHz, $CDCl_3$): 7.31 (d, J=2.1 Hz, 1H), 7.17 (d, J=2.1 Hz, 1H), 3.88 (s, 3H), 3.53 (m, 4H), 3.37 (br m, 4H), 2.35 (s, 3H), 2.30 (s, 3H). ESMS calcd for $C_{14}H_{19}Cl_2NO_2$: 303.1; Found: 304.1 (M+H)+.

A suspension of methyl 2-bis(2'-chloroethyl)amino-3,5-dimethylbenzoate (5.6 g, 0.018 mol) in concentrated HCl (37% w/w in $H_2O$, 150 mL) was heated to reflux under $N_2$ for 8 hours. The reaction mixture was treated with ice/$H_2O$ (200 mL), extracted with chloroform (3×150 mL). The organic solution was concentrated to give a white solid (5.1 g, 96%). $^1H$ NMR (300 MHz, $CDCl_3$): 8.01 (d, J=1.5 Hz, 1H), 7.23 (dd, J=1.5, 0.6 Hz, 1H), 3.6 (m, 8H), 2.43 (s, 3H), 2.35 (s, 3H). ESMS calcd for $C_{13}H_{17}Cl_2NO_2$: 289.1.

Part (3) Coupling of intermediates from parts (1) and (2)

An acetone solution (15 mL) of 2-bis(2'-chloroethyl)amino-3,5-dimethylbenzoic acid (0.45 g, 1.551 mmol) and was heated to reflux under $N_2$ in the presence of potassium carbonate (1.5 g) and sodium iodide (1.0 g). To it was added slowly an acetone (5 mL) solution of 2-chloromethyl-3,5,6-trimethylbenzoquinone (0.45 g, 2.413 mmol). After refluxing for 20 minutes, the reaction mixture was cooled to room temperature, diluted with $H_2O$ (50 mL), extracted with ethyl acetate (50 mL). The organic layer was washed with $H_2O$ (50 mL), dried over magnesium sulfate, and concentrated to an oil. Flash chromatography purification on silica gel furnished the product as sticky oil (0.52 g, 76%). $^1H$ NMR (300 MHz, $CDCl_3$): 7.25 (d, J=2.1 Hz, 1H), 7.17 (d, J=2.1 Hz, 1H), 5.24 (s, 2H), 3.49 (m, 4H), 3.38 (br m, 4H), 2.33 (s, 3H), 2.28 (s, 3H), 2.20 (s, 3H), 2.07 (s, 3H), 2.06 (s, H). ESMS calcd for $C_{23}H_{27}Cl_2NO_4$: 451.1; Found: 452.2 (M+H)+.

EXAMPLE 5

Synthesis of Compound 5

(1) See part (1) of Example 1, using 2-(2-acetoxyethyl)-benzoquinone as the starting material.

(2) See part (2) of Example 1, using 4-nitrobenzoic acid as the starting material.

(3) A dioxane (6 mL) solution of 2-chloromethyl-5-(2'-acetoxyethyl)benzoquinone (110 mg, 0.453 mmol) and 4-bis (2'-chloroethyl)aminobenzoic acid (80 mg, 0.305 mmol) was stirred in the presence of potassium carbonate at room temperature for 5 hours. The reaction mixture was diluted with hexanes (15 mL), filtered through a pad of celite. The organic phase was concentrated to an oil. Flash chromatographic purification on silica gel furnished the product as a yellow solid (18 mg, 12%). $^1$H NMR (300 MHz, CDCl$_3$): 7.97 (d, J=9.0 Hz, 2H), 6.80 (m, 4H), 5.20 (d, J=1.8 Hz, 2H), 4.26 (t, J=6.3 Hz, 2H), 3.83 (t, J=6.6 Hz, 4H), 3.68 (t, J=6.6 Hz, 2H), 2.76 (dt, J=6.0, 1.2 Hz, 2H), 2.03 (s, 3H). ESMS calcd for $C_{22}H_{23}Cl_2NO_6$: 467.1; Found: 490.0 (M+Na)$^+$.

EXAMPLE 6

Synthesis of Compound 6

(1) See part (1) of Example 1 for an analogous procedure for the synthesis of 2,3-dimethylbenzoquinone.
(2) See part (2) of Example 1.
(3) 3-Bis(2'-chloroethyl)amino-4-methoxybenzoic acid (180 mg, 0.618 mmol) was dissolved in acetone (10 mL) and heated to reflux in the presence of potassium carbonate (0.58 g).
To it was added dropwise an acetone solution (5 mL) of 2,3 -bischloromethyl-5,6-dimethylbenzoquinone (75 mg, 0.323 mmol). The reaction mixture was cooled to room temperature, diluted with ethyl acetate (15 mL), washed with aqueous potassium carbonate (2×50 mL), dried over magnesium sulfate, and concentrated to an oil. Flash chromatography purification on silica gel furnished the product as sticky oil (85 mg, 37%). $^1$H NMR (300 MHz, CDCl$_3$): 7.59 (m, 4H), 6.75 (d, J=9.0 Hz, 2H), 5.39 (s, 4H), 3.86 (s, 6H), 3.48 (m, 16H), 2.08 (s, 6H). ESMS calcd for $C_{34}H_{38}Cl_4N_2O_8$: 742.1; Found: 789.1 (M+2Na—H)$^+$.

EXAMPLE 7

Synthesis of Compound 7

(1) See part (1) of Example 1.
(2) Synthesis of methyl 4-bis(2'-chloroethyl)amino-3-(2'-(2"-methoxyethoxy)ethoxy)benzoic acid A slurry of methyl 3-hydroxy-4-nitrobenzoate (5.5 g, 0.028 mol), 1-Bromo-2-(2-methoxyethyoxy)ethane (10.0 g, 0.055 mol) and potassium carbonate (20 g) in DMF (100 mL) was stirred at 90–100° C. for 2 hours. The reaction mixture was cooled to room temperature, diluted with H$_2$O (400 mL). The resulting solid was collected by filtration, washed with H$_2$O (100 mL), and dried to give the product as a white solid (6.2 g, 74%). $^1$H NMR (300 MHz, CDCl$_3$): 7.82 (d, J=8.1 Hz, 1H), 7.78 (d, J=1.2 Hz, 1H), 7.69 (dd, J=8.1, 1.2 Hz, 1H), 4.33 (t, J=4.5 Hz, 2H), 3.95 (s, 3H), 3.92 (t, d, J=4.8 Hz, 2H), 3.73 (m, 2H), 3.55 (m, 2H), 3.38 (s, 3H). ESMS calcd for $C_{13}H_{17}NO_7$: 299.1; Found: 300.1 (M+H)$^+$.

A methanol solution (200 mL) of methyl 3-(2'-(2"-methoxyethoxy)ethoxy)-4-nitrobenzoate (6.0 g, 0.020 mol) was stirred at room temperature in the presence of 10% Pd-C and acetic acid (10 mL) under H$_2$ atmosphere for 20 h. The reaction mixture was filtered through Celite, concentrated to give an off-white solid (5.0 g, 93%). $^1$H NMR (300 MHz, CDCl$_3$): 7.55 (d, J=8.7, 2.4 Hz, 1H), 7.47 (d, J=1.8 Hz, 1H) 6.67 (d, J=8.7 Hz, 1H), 4.22 (t, J=4.8 Hz, 2H), 3.87 (m, 2H), 3.85 (s, 3H), 3.70 (t, J=4.8 Hz, 2H), 3.58 (t, J=4.8 Hz, 2H), 3.39 (s, 3H). MS calcd for $C_{13}H_{19}NO_5$: 269.1; Found: 270.1 (M+H)$^+$.

The reaction mixture methyl 4-amino-3-(2'-(2"-methoxyethoxy)ethoxy)benzoate (5.0 g, 18.6 mmol) and ethylene oxide (8.8 g, 200 mol) in acetic acid (150 mL) was stirred at room temperature for 12 hours. It was diluted with H$_2$O (300 mL), extracted with chloroform/methanol (95/5, 4×200 mL). The organic solution was concentrated to off-white oil (6.1 g, 92%). $^1$H NMR (300 MHz, CDCl$_3$): 7.62 (dd, J=8.1, 2.1 Hz, 1H), 7.52 (d, J=2.1 Hz, 1H), 7.05 (d, J=7.2 Hz, 1H), 4.22 (m, 4H), 3.89 (s, 3H), 3.9–3.8 (m, 4H), 3.68 (m, 6H), 3.58 (m, 2H), 3.38 (m, 2H), 3.37 (s, 1H). ESMS calcd for $C_{17}H_{27}NO_7$: 357.2; Found: 358.3 (M+H)$^+$.

Thionyl chloride (5.1 mL, 68 mmol) was added slowly to a benzene solution (100 mL) of methyl 4-bis(2'-hydroxythyl)amino-3-(2'-(2"-methoxyethoxy)ethoxy) benzoate (5.0 g, 13.3 mol) stirred at room temperature. After the addition, the reaction was stirred at room temperature for 16 hours. The reaction mixture was treated with ice/H$_2$O (500 mL) and extracted with ethyl acetate (2×300 mL). The combined ethyl acetate solution was washed with sodium bicarbonate (20 mL), H$_2$O (50 mL), dried over sodium sulfate, and concentrated to furnish the product as off-white oil (3.9 g, 74%). $^1$H NMR (300 MHz, CDCl$_3$): 7.58 (dd, J=8.7, 2.1 Hz, 1H), 7.49 (d, J=2.1 Hz, 1H), 6.88 (d, J=8.1 Hz, 1H), 4.18 (m, 2H), 3.87 (m, 2H), 3.86 (s, 3H), 3.69 (m, 2H), 3.63 (m, 8H), 3.56 (m, 2H), 3.37 (s, 3H). ESMS calcd for $C_{17}H_{25}Cl_2NO_5$: 393.1; Found: 394.2 (M+H)$^+$.

A suspension of Synthesis of methyl 4-bis(2'-chloroethyl) amino-3-(2'-(2"-methoxyethoxy)ethoxy)benzoate (3.0 g, 7.64 mmol) in concentrated HCl (37% w/w in H$_2$O, 50 mL) was heated to reflux under N$_2$ for 2 hours. The reaction mixture was treated with ice/H$_2$O (100 mL), extracted with chloroform (2×100 mL). The organic solution was concentrated to give a white solid (2.8 g, 97%). $^1$H NMR (300 MHz, CDCl$_3$): 7.68 (dd, J=8.4, 2.1 Hz, 1H), 7.55 (d, J=2.1 Hz, 1H), 6.92 (d, J=8.7 Hz, 1H), 4.22 (m, 1H), 3.89 (m, 2H), 3.67 (m, 10H), 3.62 (m, 2H), 3.39 (s, 3H). ESMS calcd for $C_{16}H_{23}Cl_2NO_5$: 379.1; Found: 408.2 (M–H)$^+$.

(3) Coupling of intermediates from parts (1) and (2)

The same procedure as described in part (3) in Example 1 is used. $^1$H NMR: δ7.58 (dd, J=8.7, 2.1 Hz, 1H), 7.9 (d, J=2.1 Hz, 1H), 6.88 (d, J=8.1 Hz, 1H), 5.26 (s, 2H), 0.18 (m, 2H), 3.87 (m, 2H), 3.69 (m, 2H), 3.63 (m, 8H), 3.56 (m, 2H), 3.37 (s, 3H), 2.12 (s, 3H), 2.05 (s, 3H), 2.02 (s, 3H). ESMS calcd for $C_{26}H_{33}C_{12}NO_7$: 52.2; Found: 53.1 (M+H)$^+$.

The following compounds were synthesized following procedures analogous to those example as described above.

EXAMPLE 8

Synthesis of Compound 8

$^1$H NMR: δ7.59 (dd, J=8., 2.1 Hz, 1H), 7.1 (d, J=2.1 Hz, 1H), 6.88 (d, J=8. Hz, 1H), 5.23 (s, 3H), 3.87 (d, J=6.6 Hz, 2H), 2.63 (q, J=7.2 Hz, H), 3.65 (s, 8H), 1.30 (m, 1H), 1.10 (t, J=7.2 Hz, 6H), 0.68 (m, 2H), 0.38 (m, 2H). ESMS calcd for $C_{28}H_{36}Cl_2N_2O_5$: 551.2; Found: 552.1 (M+H)$^+$.

EXAMPLE 9

Synthesis of Compound 9

$^1$H NMR: δ7.58 (dd, J=8.7, 2.1 Hz, 1H), 7.49 (d, J=2.1 Hz, 1H), 6.88 (d, J=8.1 Hz, 1H), 5.06 (q, J=7 Hz, 1H), 3.92 (t, 7 Hz, 1H), 3.63 (m, 8H), 3.56 (m, 2H), 2.12 (s, 2H), 2.05 (s, 2H), 2.02 (s, 3H), 1.80 (m, 2H), 1.45 (s, 2H), 1.00 (d, J=7 Hz, 3H). ESMS calcd for $C_{26}H_{33}Cl_2NO_5$: 510.1; Found: 511.2 (M+H)$^+$.

EXAMPLE 10

Synthesis of Compound 10

$^1$H NMR: δ7.62 (dd, J=8., 2.1 Hz, 1H), 7.5 (d, J=2.1 Hz, 1H), 37.30 (d, J=Hz, 1H), 6.85 (d, J=8. Hz, 1H), 6.0 (d,

J=Hz, 1H), 625 (d, J=Hz, 1H), 5.23 (s, 2H), .50 (s, 2H), 3.85 (s, 6H), 3.65 (s, 8H), 2.05 (s, 3H), 2.00 (s, 3H). ESMS calcd for $C_{27}H_{30}Cl_2N_2O_6$: 59, 2; Found: 550.1 (M+H)$^+$.

EXAMPLE 11

Synthesis of Compound 11

$^1$H NMR: δ7.58 (dd, J=8.7, 2.1 Hz, 1H), 7.9 (d, J=2.1 Hz, 1H), 6.88 (d, J=8.1 Hz, 1H), 5.26 (s, 2H), .18 (m, 2H), 3.92 (s, 3H), 3.87 (m, 2H), 3.69 (m, 2H), 3.63 (m, 8H), 3.56 (m, 2H), 3.37 (s, 3H), 2.05 (s, 3H), 2.02 (s, 3H). ESMS calc for $C_{26}H_{33}Cl_2NO_8$: 558:2; Found: 559.1 (M+H)$^+$.

EXAMPLE 12

Synthesis of Compound 12

$^1$H NMR: δ7.52 (dd, J=8.4, 2.1 Hz, 1H), 7.7 (d, J=2.1 Hz, 1H), 7.7 (d, J=2.1 Hz, 1H), 6.86 (d, J=8.1 Hz, 1H), 5.25 (s, 2H), 3.98 (d, J=6.9 Hz, 2H), 3.60 (m, 8H), 2.82 (m, 1H), 2.25–2.1 (m, 2H), 2.18 (s, 3H), 2.05 (s, 3H), 2.0 (s, 3H), 2.0–1.7 (m, H). ESMS calcd for $C_{26}H_{33}Cl_2NO_8$: 558.2; Found; 559.1 (M+H)$^+$.

EXAMPLE 13

Synthesis of Compound 13

$^1$H NMR: δ7.59 (dd, J=8.4, 2.1 Hz, 1H), 7.1 (d, J=2.1 Hz, 1H), 6.88 (d, J=8.4 Hz, 1H)5.23 (s, 3H), 3.87 (d, J=6.6 Hz, 2H), 2.63 (q, J=7.2 Hz, H), 3.65 (s, 8H), 2.15 (s, 3H), 2.08 (s, 3H), 2.0 (s, 3H), 1.30 (m, 1H), 1.10 (t, J=7.2 Hz 6H), 0.68 (m, 2H), 0.38 (m, 2H). ESMS calcd for $C_{28}H_{36}Cl_2N_2O_5$: 551.2; Found: 552.1 (M+H)$^+$.

EXAMPLE 14

Synthesis of Compound 14

$^1$H NMR: δ7.4 (dd, J=8.7, 1.8 Hz, 1H), 7.0 (d, J=1.8 Hz, 1H), 6.75 (d, J=8.7 Hz, 1H)5.38 (s, 2H), 3.96 (t, J=6.6Hz, 2H), 3.56 (m, 8H), 2.08 (s, 3H), 2.0 (s, 3H), 1.80 (m, 2H), 1.8 (m, 2H), 0.99 (t, J=7.2Hz, 3H). ESMS calcd for $C_{25}H_{29}CL_2N_3O_5$: 522.2; Found: 523.1 (M+H)$^+$.

EXAMPLE 15

Synthesis of Compound 15

$^1$H NMR: δ7.4 (dd, J=8.7, 1.8 Hz, 1H), 7.0 (d, J=1.8 Hz, 1H), 6.75 (d, J=8.7 Hz, 1H), 5.38 (s, 2H), .67 (m, 2H), 3.96 (t, J=6.6 Hz, 2H), 3.91 (s, 3H), 3.56 (m, 8H), 2.23 (s, 3H), 2.08 (s, 3H), 1.80 (m, 2H), 1.8 (m, 2H), 0.99 (t, J=7.2 Hz, 3H), ESMS calcd for $C_{28}H_3CL_2N_2O_6$: 565.2; Found: 566.1 (M+H)$^+$.

EXAMPLE 16

Synthesis of Compound 16

$^1$H NMR: δ7.4 (dd, J=2.19, 2.19 Hz, 1H), 7.63 (m, 1H), 6.65 (d, J=8.52, 1H), 5.22 (s, 2H), 3.8 (m, 8H), 2.31 (s, 3H), 2.15 (s, 3H)2. (s, 3H), 2.0 (s, 3H). ESMS Calc for $C_{22}H_{25}CL_2NO$: 38.31.; Found: 39.0 (M+H)$^+$.

EXAMPLE 17

Synthesis of Compound 17

$^1$H NMR: δ7.76 (dd, J=8. and 1.8 Hz, 1H), 7.68 (d, J=1.8 Hz, 1H), 6.98 (d, J=8. Hz, 1H), 5.30 (s, 2H), 3.53 (brs, 8H), 2.35 (s, 3H), 2.18 (s, 3H), 2.0 (s, 3H), 2.02 (s, 3H). ESMS calcd for $C_{22}H_{25}Cl_2NO$: 22.1; Found: 823.1(M+H)$^+$.

EXAMPLE 18

Synthesis of Compound 18

$^1$H NMR: δ7.70 (dd, J=8., 1.8 Hz, 1H), 7.65 (d, J=1.8 Hz, 1H), 6.86 (d, J=8 Hz, 1H), 5.25 (s, 3H), 3.90 (s, 3H), 3.50 (s, 8H), 2.18 (s, 3H), 2.06 (s, 3H), 2.05 (s, 3H). ESMS calcd for $C_{22}H_{25}C_{;2}NO_5$: 53.1; Found: 5.1 (M+H)$^+$.

EXAMPLE 19

Synthesis of Compound 19

$^1$H NMR: δ7.76 (dd, J=8. and 1.8 Hz, 1H), 7.68 (d, J=1.8 Hz, 1H), 6.98 (d, J=8. Hz, 1H), 5.22 (s, 2H), 3.68–3.80 (brm, H), 3.53 (br s, 8H), 3.6 (t, J=5.0 Hz, 2H), 2.58–2.6 (bm, H), 2.0 (s, 3H), 2.02 (s, 3H), 1.86 (J=5.0 Hz, 2H), 1.30 (m, 10H), 0.89 (t, J=6.9 Hz, 3H). ESMS calcd for $C_{31}HCl_2N_2O_6$: 611.2; Found: 612.1 (M+H)$^+$.

EXAMPLE 20

Synthesis of Compound 20

$^1$H NMR: b 7.4 (dd, J=2.19, 2.19 Hz, 1H), 7.63 (m, 1H), 6.65 (d, J=8.52, 1H), 5.22 (s, 2H), 3.90 (s, 3H), 3.8 (m, 8H), 2.0 (t, J=7 Hz), 2.15 (s, 3H), 2.0 (s.3H), 2.0 (s, 3H), 1.65 (m, 2H), 1.3 (m, 2H), 0.92 (t, J=8 Hz). ESS Calc for $C_{26}H_{32}Cl_2N_2O_6$: 539.2; Found: 50.1 (M+H)$^+$.

EXAMPLE 21

Synthesis of Compound 21

$^1$H NMR: δ7.4 (dd, J=2.19, 2.19 Hz, 1H), 7.63 (m, 1H), 7.20 (m, 5H), 6.65 (d, J=8.52, 1H), 5.22 (s, 2H), 5.18 (s, 2H), 3.80 (s, 6H), 3.8 (m, 8H), 2.15 (s, 3H), 2. (s, 3H), 2.0 (s, 3H). ESMS Calc for $C_{30}H_{33}Cl_2N_3O_6$: 602.2; Found: 603.1 (M+H)$^+$.

EXAMPLE 22

Synthesis of Compound 22

$^1$H NMR: δ8.20 (d, J=7.0 Hz, 1H), 8.11 (d, J=7.0 Hz, 1H), 7.70 (dd, J=8., 1.8 Hz), 7.65 (d, J=1.8 Hz, 1H), 7.53 (m, 2H), 6.86 (d, J=8. Hz, 1H), 5.25 (s, 3H), 3.90 (s, 3H), 3.50 (s, 8H), 2.18 (s, 3H). ESMS cacld for $C_2H_{23}Cl_2NO_5$: 76.1; Found: 77.0 (M+H)$^+$.

EXAMPLE 23

Synthesis of Compound 23

$^1$H NMR: δ7.76 (dd, J=8.4, 1.8 Hz, 1H), 7.55 (d, J=1.8 Hz, 1H), 7.02 (s, 1H), 6.86 (d, J=8. Hz, 1H), 5.23 (s, 2H), 3.90 (S, 3H), 3.50 (s, 8H), 2.26 (s, 3H), 2.03 (s, 3H). ESMS cacld for $C_{23}H_{23}Cl_2NO_6$: 80.1; Found: 81.2 (M+H)$^+$.

EXAMPLE 24

Synthesis of Compound 24

$^1$H NMR: δ7.4 (dd, J=8.7, 1.8 Hz, 2H), 7.0 (d, J=1.8 Hz, 2H), 6.75 (d, J=8.7 Hz, 2H), 5.38 (s, H), 3.96 (t, J=6.6 Hz, H), 3.56 (m, 16H), 1.80 (sexet, J=7.5 Hz, H), 1.8 (sexet, J=7.5 Hz, H), 0.99 (t, J=7.2 Hz, 6H). ESMS calcd for $C_0H_{50}ClN_2O_8$: 826.2; Found: 827.1(M+H)$^+$.

EXAMPLE 25

Synthesis of Compound 25

$^1$H NMR δ7.80 (dd, J=2.19 and 2.19 Hz, 1H), 7.53 (m, 1H), 6.6 (d, J=8.52, 1H), 5.22 (s, 2H), 3.80 (s, 3H), 3.8 (m, 8H), 2.3 (s, 3H), 2.31 (s, 3H), 2.15 (s, 3H), 2. (s, 3H). ESMS Calc for $C_2H_{28}Cl_2N_2O$: 08.2; Found: 09.1 (M+H)$^+$.

EXAMPLE 26

Biological Testings

Human mammary carcinoma (MDA-35) tumor cells, which were adapted to grow as solid tumors in nude mice, were implanted by injection of a tumor cell suspension (3–5×10$^6$ cells) in media into the fat pads of female nude mice (Taconic Labs). Five mice per group were used. When tumors were palpable, two to three weeks after implantation, animals were injected with the cytotoxic compounds of this invention intravenously on a three times per week schedule at the MTD. Tumor volumes were measured with calipers weekly during and for two weeks after dosing was suspended. The volume of tumors, assumed to be hemi-ellipsoid in shape, was calculated using the equation:

$$\text{Volume} = \frac{1}{2}(L/2 \times W/2 \times H)/3\,\pi$$

where L=length, W=width and H=height of the tumor. Animals were weighed and general health was monitored during the course of the assay. When tumors reached approximately 15 mm in diameter (about 800 mm$^3$) or necrotic or animals became moribund, the animals were euthanized by $CO_2$ asphyxiation.

The volumes of tumors in the animals which were treated with various cytotoxic compounds of this invention were calculated and compared to those obtained from the animals which were treated with chlorumbucil (an aromatic nitrogen mustard-containing anticancer drug) and also with those obtained from the untreated animals. Tested cytotoxic compounds of this invention demonstrated unexpectedly high efficacy in inhibiting tumor growth.

OTHER EMBODIMENTS

From the above description, one skilled in the art can easily ascertain the essential characteristics of the present invention, and without departing from the spirit and scope thereof, can make various changes and modifications of the invention to adapt it to various usages and conditions. For example, linkers that contain heteroatoms, e.g., —CH=N—CH$_2$— or —N=N—CH$_2$—, although not described above, can also function as a part of the conjugated system of a cytotoxic compound of this invention. Thus, other embodiments are also within the claims.

What is claimed is:

1. A quinone derivative of the following formula:

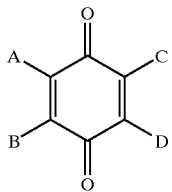

wherein each of A and B, independently, is —R$^1$, —R—NR$^1$R$^2$, —O—R$^1$, —R—OH, —C(=O)O—R$^1$, —R—O—C(=O)R$^1$, —C(=O)—NR$^1$R$^2$, —R—NR$^1$—C(=O)R$^2$, —SO$_2$—NR$^1$R$^2$, —N=SO$_2$, —S—R$^1$, or —L—W—Ph—N(CH$_2$CH$_2$X)$_2$; C and D together form an imidazolyl ring fused with the quinone ring at the 4-position and 5-position carbon atoms of the imidazolyl ring; in which each R, independently, is alkyl or is a bond; each of R$^1$ and R$^2$, independently, is hydrogen, alkyl, alkenyl, aryl, aralkyl, heteroaryl, or heteroaralkyl; L is —(CR$^3$=CR$^4$)n—CR$^5$R$^6$—, where each of R$^3$, R$^4$, R$^5$, and R$^6$ independently, is hydrogen, alkyl, alkenyl, aryl, aralkyl, heteroaryl, heteroaralkyl, or —(O-alkyl)1–5; and n is 0, 1, or 2; W is —O—C(=O)—, —O—C(=O)—NR$^1$—, or —O—C(=O)O—; Ph is a phenyl group, optionally substituted with alkyl, alkenyl, aryl, aralkyl, heteroaryl, heteroaralkyl, —R—NR$^1$R$^2$, —OH, —(O-alkyl)1–5, —O-aryl, —O-aralkyl, —O-heteroaryl, —O-heteroaralkyl, —R—OH, —C(=O)O—R$^1$, —O—C(=O)R$^1$, —C(=O)—NR$^1$R$^1$, —NR$^1$—C(=O)R$^2$, —NR$^1$—C(=O)O—R$^2$, —NR$^1$—C(=O)—NR$^1$R$^2$, or —S—R$^1$; and X is a halo;

provided that if none of A and B is —L—W—Ph—N(CH$_2$CH$_2$X)$_2$, then the imidazolyl ring is substituted at the 2-position carbon atom with —L—W—Ph—N(CH$_2$CH$_2$X)$_2$; or a salt thereof.

2. The quinone derivative of claim 1, wherein W is —O—C(=O)—, X is chloro, and n is 0; or a salt thereof.

3. The quinone compound of claim 1, wherein none of A and B is —L—W—Ph—N(CH$_2$CH$_2$X)$_2$; or a salt thereof.

4. The quinone compound of claim 3, wherein W is —O—C(=O)—, X is chloro, n is 0, W and —N(CH$_2$CH$_2$X)$_2$ are at a para or meta position with respect to each other, and Ph is substituted with alkyl, alkenyl, aryl, aralkyl, heteroaryl, heteroaralkyl, —(O-alkyl)$_{1-5}$, —O-aryl, —O-aralkyl, —O-heteroaralkyl, or —O-heteroaryl at a position ortho to —N(CH$_2$CH$_2$X)$_2$; or a salt thereof.

5. The quinone compound of claim 1, wherein W is —O—C(=O)—, X is chloro, and n is 0; or a salt thereof.

6. The quinone compound of claim 5, wherein W and —N(CH$_2$CH$_2$X)$_2$ are at a para or meta position with respect to each other; or a salt thereof.

7. The quinone compound of claim 6, wherein Ph is substituted with alkyl, alkenyl, aryl, aralkyl, heteroaryl, heteroaralkyl, —(O-alkyl)$_{1-5}$, —O-aryl, —O-aralkyl, —O-heteroaryl, or —O-heteroaralkyl at a position ortho to —N(CH$_2$CH$_2$X)$_2$; or a salt thereof.

8. The quinone compound of claim 1 of the following structure:

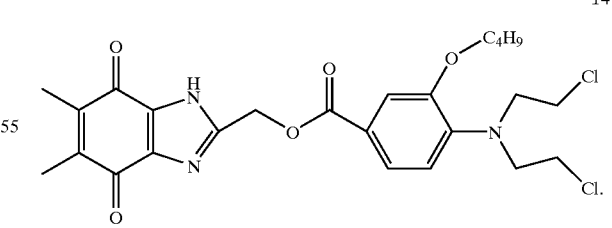

* * * * *